United States Patent
Kunisch et al.

(10) Patent No.: US 6,217,642 B1
(45) Date of Patent: *Apr. 17, 2001

(54) BENZOTHIOPHENE-2-CARBOXAMIDE S,S-DIOXIDES FOR USE IN ANTI-FOULING APPLICATIONS

(75) Inventors: Franz Kunisch, Odenthal; Martin Kugler, Leichlingen; Heinrich Schrage, Krefeld; Hans-Ludwig Elbe, Wuppertal, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,364
(22) PCT Filed: Sep. 9, 1996
(86) PCT No.: PCT/EP96/03941
  § 371 Date: Mar. 11, 1998
  § 102(e) Date: Mar. 11, 1998
(87) PCT Pub. No.: WO97/11131
  PCT Pub. Date: Mar. 27, 1997

(30) Foreign Application Priority Data

Sep. 20, 1995 (DE) .............................. 195 34 868

(51) Int. Cl.[7] .............................. C09D 5/16; A61K 31/38; C07D 333/70

(52) U.S. Cl. .................. 106/18.33; 424/405; 424/78.09; 504/154; 514/378; 514/443; 548/240; 548/525; 549/53; 549/55; 549/57

(58) Field of Search .................. 106/18.33; 514/212, 514/228.2, 233.5, 253, 324, 378, 422, 443; 424/405, 78.09; 504/154, 219, 221, 225, 235, 249, 271, 287, 289; 540/596; 544/58.4, 145, 146, 376; 546/202; 548/240, 525; 549/53, 55, 57

(56) References Cited

U.S. PATENT DOCUMENTS 5,244,893 * 9/1993 Elbe et al. ............................ 514/212
5,622,546 * 4/1997 Elbe et al. ......................... 106/18.33

FOREIGN PATENT DOCUMENTS

| 266738 | 5/1988 | (EP) . |
| 512349 | 11/1992 | (EP) . |
| 556949 | 8/1993 | (EP) . |
| 9408904 | 4/1994 | (WO) . |
| 9506091 | 3/1995 | (WO) . |

OTHER PUBLICATIONS

Stewart, V.N., "Barnacles", May 1990 (Florida Marine Research Institute Educational Brochure).

* cited by examiner

*Primary Examiner*—Anthony Green
(74) *Attorney, Agent, or Firm*—Norris McLaughlin & Marcus

(57) ABSTRACT

A method and composition for protection against fouling of objects which come into contact with sea water or brackish water comprising a benzothiophene-2-carbomide S,S-dioxide as the essential component are described.

2 Claims, No Drawings

BENZOTHIOPHENE-2-CARBOXAMIDE S,S-DIOXIDES FOR USE IN ANTI-FOULING APPLICATIONS

This application is a 371 of PCT/EP96/03941, which was filed on Sep. 9, 1996.

The present invention relates to a method and composition for protecting objects from fouling, in particular ships' hulls, screens, nets, structures, wharfs and signalling installations, which come into contact with sea-water or brackish water.

Fouling by species of the group Lepadomorpha (goose barnacles), such as various Lepas and Scalpellum species, or by species of the group Balanomorpha (acorn bamacles), such as Balanus or Pollicipes species, increases the frictional resistance of ships and as a result, due to increased consumption of energy and frequent periods in dry dock, leads to a significant increase in operating costs.

In addition to fouling by algae, for example Ectocarpus sp. and Ceramium sp., fouling by sessile Entomossra groups, called collectively by the name Cirripedia (barnacle crabs) is of special importance in particular.

Benzothiophene-2-carboxamide S,S-dioxides (BCDs), a process for their preparation and their fungicidal action are known (DE-A41 15 184). Their activity against phytopathogenic fungi and dermatophytes is described in particular. It is furthermore stated that BCDs are suitable for protection of industrial materials against microbial change or destruction.

Their use for treatment of mould-resistant emulsion paints is known from U.S. Pat. No. 5,622,546, equivalented to EP 714420.

It has now been found, surprisingly, that BCDs not only attack the species of moulds which usually grow on paints, but also have an outstanding antifouling action.

The application therefore relates to the use of benzothiophene-2-carboxamide S,S-dioxides for protection of objects against fouling.

The compounds used as antifouling active compounds in this invention are represented by the formula (I)

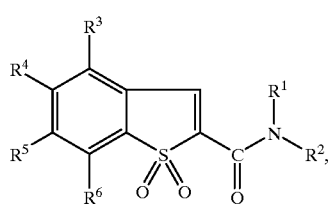

(I)

in which
R$^1$ represents optionally substituted alkyl, or represents alkenyl or alkinyl, or represents in each case optionally substituted cycloalkyl or cycloalkylalkyl, or represents in each case optionally substituted aralkyl, aralkenyl, aralkinyl or aryl,
R$^2$ represents hydrogen, or represents optionally substituted alkyl, or
R$^1$ and R$^2$, together with the nitrogen atom to which they are bonded, represent an optionally substituted heterocyclic radical and
R$^3$, R$^4$, R$^5$ and R$^6$ independently of one another each represent hydrogen, halogen, cyano, nitro, alkyl, alkoxy, alkylthio, halogenoalkyl, halogenoalkoxy or halogenoalkylthio.

Compounds of the formula (I) which are preferably used are those in which

R$^1$ represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl or n- or i-octadecyl, or represents allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl or propoxycarbonylpropyl; or further represents cyclopropyl, cyclopropylmethyl, cyclopropylethyl, cyclopropylpropyl, cyclopentyl, cyclopentylmethyl, cyclopentylethyl, cyclpentylpropyl, cyclohexyl, cyclohexylmethyl, cyclohexylethyl or cyclohexylpropyl, in each case optionally substituted in the cycloalkyl part once to four times in an identical or different manner by fluorine, chlorine, bromine, methyl, ethyl, n- or i-propyl, chloromethyl, dichloromethyl or trifluoromethyl; or furthermore represents phenylalkyl, phenylalkenyl, phenylalkinyl, phenyl or naphthyl, in each case optionally substituted in the aryl part once to three times in an identical or different manner and in each case, where appropriate, having up to 6 carbon atomns in the straight-chain or branched alkyl or alkenyl or alkinyl part, possible substituents on the aryl in each case being: fluorine, chlorine, bromine, hydroxy, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, tifluoromethoxy, trifluoromethylthio, methylcarbonyl, ethylcarbonyl, methoxycarbonyl, ethoxycarbonyl, aminocarbonyl, N-methylaminocarbonyl, N,N-dimethylaminocarbonyl, N-ethylaminocrbonyl, N,N-diethylaminocarbonyl, N-formylamino, N-acetylamino, N-methyl-N-formylamino, N-methyl-N-acetyl-amino, N-ethyl-N-formylamino, N-ethyl-N-acetyl-amino, methoximinomethyl, methoximinoethyl, ethoximinomethyl, ethoximinoethyl or phenyl which is optionally substituted once to three times in an identical or different manner by fluorine, chlorine, bromine, methyl and/or ethyl, R$^2$ represents hydroge, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dimethylaminomethyl, diethylaminomethyl, dipropylaminomethyl, dimethylaminoethyl, diethylaminoethyl, dipropylaminoethyl, dimethylaminopropyl, diethylaminopropyl or dipropylaminopropyl or $R^1$ and $R^2$, together with the nitrogen atom to which they are bonded, represent a heterocyclic radical of the formula

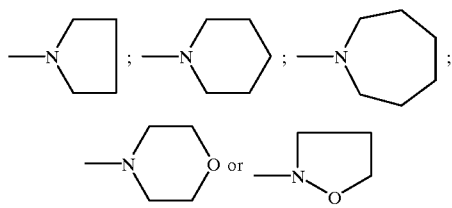

which is optionally substituted once, twice or three times by methyl and/or ethyl, and $R^3$, $R^4$, $R^5$ and $R^6$ independently of one another each represent hydrogen, fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio.

Compounds of the formula (I) which are particularly preferably used are those in which $R^1$ represents methyl, ethyl, n- or i-propyl, n-, i-, s- or t-butyl, n- or i-pentyl, n- or i-hexyl, n- or i-heptyl, n- or ioctyl, n- or i-nonyl, n- or i-ecyl, n- or i-dodecyl, n- or i-octadecyl, or represents allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, or furthermore represents cyclopropyl, cyclopropylmethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, in each case optionally substituted in the cycloalkyl part once to four times in an identical or different manner by fluorine, chlorine, bromine, methyl, ethyl, n- or i-propyl, chloromethyl, dichloromethyl or trifluoromethyl; or furthermore represents phenylalkyl, phenylalkenyl, phenylaikinyl, phenyl or naphthyl, in each case optionally substituted in the aryl part once to three times in an identical or different manner and in each case, where appropriate, having up to 6 carbon atoms in the straight-chain or branched alkyl or alkenyl or alkinyl part, possible substituents on the aryl in each case being: fluorine, chlorine, bromine, hydroxy, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methylcarbonyl, ethylcarbonyl, methoxycarbonyl, ethoxycarbonyl, or phenyl which is optionally substituted once to three times in an identical or different manner by fluorine, chlorine, bromine, methyl and/or ethyl, $R^2$ represents hydrogen, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl or ethoxypropyl, or $R^1$ and $R^2$, together with the nitrogen atom to which they are bonded, represent a heterocyclic radical of the formula

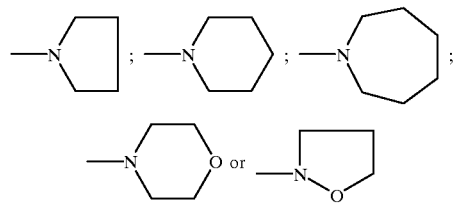

which is optionally substituted once, twice or three times by methyl and/or ethyl, and $R^3$, $R^4$, $R^5$ and $R^6$ independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio.

Compounds of the formula (I) which are especially preferably used are those in which $R^1$ represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl or n- or i-octadecyl, or represents allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl or ethoxypropyl, or furthermore represents cyclopropylmethyl, cyclopropylethyl, cyclopropyipropyl, cyclopentyl, cyclopentylmethyl, cyclopentylethyl, cyclopentylpropyl, cyclohexyl, cyclohexylmethyl, cyclohexylethyl or cyclohexylpropyl, in each case optionally substituted in the cycloalkyl part once to four times in an identical or different manner by fluorine, chlorine, bromine, methyl, ethyl or n- or i-propyl; or furthermore represents phenylalkyl, phenylalkenyl, phenylalkiyl, phenyl or naphthyl, in each case optionally substituted in the aryl part once to three times in an identical or different manner and in each case, where appropriate, having up to 6 carbon atoms in the straight-chain or branched alkyl or alkenyl or alkinyl part, possible substituents on the aryl in each case being: fluorine, chlorine, bromine, hydroxy, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio, or phenyl which is optionally substituted once to three times in an identical or different manner by fluorine, chlorine, bromine, methyl and/or ethyl, $R^2$ represents hydrog methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl or cyanopropyl, or $R^1$ and $R^2$, together with the nitrogen atom to which they are bonded, represent a heterocyclic radical of the formula

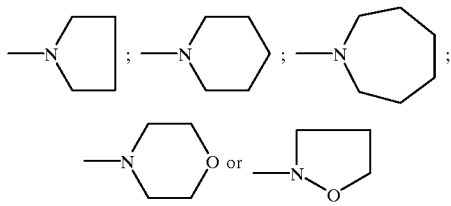

which is optionally substituted once, twice or three times by methyl and/or ethyl, and $R^3$, $R^4$, $R^5$ and $R^6$ independently of one another in each case represent hydrogen, fluorine, chlorine, bromine, cyano, nitro, methyl, ethyl, n- or i-propyl, n-, i-, s- or t-butyl, methoxy, methylthio, ethylthio, trifluoromethyl, trifluoromethoxy or trifluoromethylthio.

The benzothiophene-2-carboxamide S,S-dioxides are accessible by the processes mentioned in EP 0 512 349.

The BCDs can be used as individual active compounds or else in combination with active compounds usually employed in the antifouling sector. These can preferably be heavy metals, such as tin or Cu, or heavy metal compounds, such as, for example, bis(trialkyltin) sulphides, tri-n-butyltin laurate, tri-n-butyltin chloride, copper(I) oxide, triethyltin chloride, tri-n-butyl(2-phenyl4-chlorophenoxy)-tin, tributyltin oxide, molybdenum disulphide, antimony oxide, polymeric butyl titanate, phenyl-bispyridine)-bismuth chloride, tri-n-butyltin fluoride, manganese ethylenebisdithiocarbamate, zinc dimethyldithiocarbamate, zinc ethylenebisdithiocarbamate, the zinc salt or copper salt of 2-pyridinethiol 1-oxide, bisdimethyldithiocarbamoylzinc ethylenebisdithiocarbamate, zinc oxide, copper(I) ethylene-bis-dithiocarbamate, copper thiocyanate, copper naphthenate and tributyltin halides.

The action spectrum of the N-alkylbenzothiophene-2-carboxamide S,S-dioxides is extended further or particular effects are achieved by these combinations of active compounds. Synergistic effects are obtained in many cases. The synergistic effect manifests itself particularly clearly if the active compound combinations are present in certain weight ratios. However, the weight ratios of the active compounds in the active compound combinations can vary within a relatively wide range.

Other combination partners which are suitable for the antifouling compositions according to the invention are, preferably, algicides, fungicides, insecticides, molluscicides and bactericides, such as, for example:

Triazoles:
azaconazole, bromuconazole, cyproconazole, dichlobutrazole, diniconazole, hexconazole, metconazole, penconazole, propiconazole, tebuconazole, amitrole, azocyclotin, epoxyconazole, bitertanol, difenoconazole, fenbuconazole, fenchiorazole, fenethanil, fluquinconazole, flusilazole, flutriafol, imibenconazole, isozofos, myclobutanil, paclobutral, (±)-cis-1-(4-chlorophenyl)2-1H-1,2,4triazol-1-yl)-cycloheptanol, tetraconazole, triadimefon, triadimenol, triapenthenol, triflumizole, triticonazole, uniconazole and metal salts and acid adducts thereof.

Imidazoles:
imazalil, pefurazoate, prochloraz, triflumizole.

Thiazolecarboxanilides such as 2',6'-dibromo-2-methyl4-trifluoromethoxy4'-trifluoromethyl-1,3-thiazole-5-carboxanilide and metal salts and acid adducts thereof.

Succinate dehydrogenase inhibitors, such as:
fenfuram, furcarbanil, cyclafluramid, furmecyclox, Seedvax, metsulfovax, pyracarbolid, oxycarboxin, Shirlan, mebenil (mepronil), benodanil, flutolanil (Moncut);

Naphthalene derivatives, such as:
terbinafme, naftifine, butenafine;

Sulfenamides, such as dichlofluanid, tolylfluanid, folpet, fluorfolpet; captan, captofol;

Benzimidazoles, such as carbendazirm, benomyl, furahiocarb, fuberidazole, thiophanate-methyl, thiabendazole or salts thereof;

Morpholine derivatives, such as tridemorph, fenpropimorph, falimorph, dimethomorph, dodemorph; aldimorph, fenpropidin and its arylsulphonic acid salts, such as, for example, p-toluenesulphonic acid and p-dodecylphenyl-sulphonic acid;

Dithiocarbamates, such as cufraneb, ferbam, mancopper, mancozeb, maneb, metam, metiram, thiran zeneb, ziram;

Benzothiazoles, such as 2-mercaptobenzothiazole;

Benzamides, such as 2,6dichloro-N(4-trifluoromethylbenzyl)-benzamide;

Boron compounds, such as boric acid, boric acid esters, borax;

Formaldehyde and compounds which split off formaldehyde, such as benzyl alcohol mono-(poly)-hemiformal, oxazolidines, hexa-hydro-S-triazines, N-methylolchloroacetamide, paraformaldehyde, nitropyrin, oxolinic acid, tecloftalam;

Tris-N-(cyclohexyldiazeniumdioxy)-aluminium, N-(cyclo-hexyldiazeniumdioxy)-tributyltin or K salts, bis-N-cyclohexyldiazeniumdioxy)-copper.

N-methylisothiazolin-3-one, 5-chloro-N-methylisothiazolin-3-one, 4,5-dichloro-N-octylisothiazolin-3-one, N octyl-isothiazolin-3-one, 4,5-trimethylene-isothiazolinones, 4,5-benzisothiazolinones;

Aldehydes, such as cinnamaldehyde, formaldehyde, glutaraldehyde, β-bromocinnamaldehyde; thiocyanates, such as thiocyanatomethylthiobenzothiazole, methylene bisthiocyanate and the like;

quaternary ammonium compounds, such as benzyldimethyltetradecylammonium chloride, benzyldimethyl-dodecylammonium chloride, didecyldimethylammonium chloride;

Iodine derivatives, such as diiodomethyl p-tolyl sulphone, 3-iodo-2-propinyl alcohol, 4-chloro-phenyl 3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butyl-carbamate, 3-iodo-2-propinyl-n-butyl-urea, 3-iodo-2-propinyl n-hexylcarbamate, 3-iodo-2-propinyl cyclohexylcarbamate, 3-iodo-2-propinyl phenylcarbamate;

Phenol derivatives, such as tribromophenol, tetrachlorophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol and alkali metal and alkaline earth metal salts thereof.

Microbicides having an activated halogen group, such as chloroacetamide, N-methylolchloroacetamide, bronopol, bronidox, tectamer, and such as 2-bromo-2-nitro-1,3-propanediol, 2-bromio-4'-hydroxy-acetophenone, 2,2-dibromo-3-nitrile-propionamide, 1,2-dibromo-2,4-dicyanobutane, β-bromo-β-nitrostyrene;

Pyridines, such as 1-hydroxy-2-pyridinethione (and its Na, Fe, Cu, Mn, Zn salts), tetraloro-4-methylsulphonylpyridine, pyrimethanol, mepanipyrim, dipyrithione;

Metal soaps such as tin, copper or zinc naphthenate, octoate, 2-ethylhexanoate, oleate, phosphate or benzoate;

Metal salts, such as copper hydroxycarbonate, sodium dichromate, potassium dichromate, potassium chromate, copper sulphate, copper chloride, copper borate, zinc fluorosilicate, copper fluorosilicate.

Oxides, such as tributyltin oxide, $Cu_2O$, CuO, ZnO;

Dialkyldithiocarbamates such as Na and Zn salts of dialkyldithiocarbamates, tetramethylthiuram disulphide, potassium N-methyl-dithiocarbamate;

Nitriles, such as 2,4,5,6-tetrachloroisophthalodinitrile, disodium cyanodithioimidocarbamate;

Quinolines, such as 8-hydroxyquinoline and Cu salts thereof;

mucochloric acid, 5-hydroxy-2(5H)-furanone;

4,5-dichlorodithiazolinone,4,5-benzodithiazolinone,4,5-trimethylenedithiazolinone,4,5-dichloro-(3H)-1,2-dithiol-3-one, 3,5-dimethyl-tetrahydro 1,3,5-thiadiazine-2-thione;

N-(2-p-chlorobenzoylethyl)-hexaminium chloride, potassium N-hydroxymethyl-N'-methyl dithiocarbamate, 2-oxo-2-(4-hydroxy-phenyl)acetohydroximic acid chloride, phenyl 2-chloro-cyano-vinyl sulphone, phenyl 1,2-dichloro-2-cyano-vinyl sulphone;

Ag, Zn or Cu-containing zeolites, by themselves or included in polymeric active compounds.

Mixtures having a good action are furthermore also prepared with the following active compounds:

Fungicides:
Methyl (E)-methoximino[α-(o-tolyloxy)-o-tolyl] acetate, methyl (E)2-{2-[6-(2-cyanophenoxy)-pyrimidineyl-4-yl-oxy]phenyl}-3-methoxyacrylate,
acypetacs, 2-aminobutane, ampropylfos, anilazine, benalaxyl, bupirimate, chinomethionate, chloroneb, chlozolinate, cymoxanil, dazomet, diclomezine, dichloram, diethofencarb, dimetirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, oflurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thcyofen, thiophanate-methyl, tolclofos-methyl, triazoxide, trichlamide, tricyclazole, triforine, vinclozolin.

Insecticides:
Phosphoric acid esters, such as azinphos-ethyl, azinphos-methyl, α-1(4-chlorophenyl)-4-(O-ethyl, S-propyl)phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

Carbamates, such as aldicarb, bendiocarb, α-2-(1-methylpropyl)-phenyl methylcarbamnate, butocarboxim, butoxycarboxim, carbaryl, barbofuran carbosulfan, cloethocab, isoprocarb, methomyl, oxamyl, primicarb), promecarb), propoxur and thiodicarb;

Organosilicon compounds, preferably dimethyl (phenyl)silyl-methyl 3-phenoxybenzyl ethers, such as dimethyl-(4-ethoxyphenyl)-silylmethyl 3-phenoxy-benzyl ether or (dimethylphenyl)-silyl-methyl-2-phenoxy-6-pyridylmethyl ethers, such as, for example, dimethyl-(9-ethoxy-phenyl)-silylmethyl-2-phenoxy-6-pyridylmethyl ether or [(phenyl)-3-(3-phenoxyphenyl)-propyl](dimethyl)-silanes such as, for example (4-ethoxyphenyl)-[3-(4-fluoro-3-phenoxyphenyl-propyl]dimethyl-silane, silafluofen;

Pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl) cyclopropane-carboxylate, fenpropathrin, fenfluthri fenvalerte, flucythirinate, flumethrin, fluvalinate, permethrin, resmethrin and tralomethrin;

Nitroimines and nitromethylenes, such as 1-[(6-chloro-3-pyridinyl)methyl]4,5-dihydro-N-nitro-1H-imidazol-2-amine (imidacloprid), N-[(6-chloro-3-pyridyl)methyl-]$N^2$-cyano-$N^1$-methylacetamide (NI-25);

Abamectin, AC 303, 630, acephate, acrinathrin alanycarb, aldoxycarb, aldrin, amitraz, azamethiphos, Bacillus thuringiensis, phosmet, phosphamidon, phosphines, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulphuryl fluoride, tar oils, teflubenzuron, tefluthrin, temephos, terbufos, tetrachlorvinphos, tetramedirin, o-2-tert-butyl-pyrimidin-5-yl O-isopropyl phosphorothioate, thiocyclam, thiofanox, thiometon, tralomethrin, triflumuron, trimethacarb, vamidothion, verticillium lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionat, chlordane, chlorfenvinphos, chlorfluazuron, chlomephos, chloropicrin, chlorpyrifos, cyanophos, beta-cyfluhrin, alpha-cypermedirin, cyophenothrin, cyromazine, dazomet, DDT, demeton-S-methylsulphon, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mercarbam, mephosfolan, mercurous chloride, metam, Metarthizium anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, omethoate, oxydefmeton-methyl, pentachorophenol, petroleum oils, phenothrin, phenthoate, phorate;

Molluscicides:

Fentin acetate, metaldehyde, methiocarb, niclosamide, thiodicarb, trimethacarb;

Algicides;

Copper sulphate, dichlorosphen, endothal, fentin acetate, quinoclamine;

Herbicides:

Diuron, dichlorophen, endothal, fentin acetate, quinochlamine.

Synergistic effects are also to be observed for these combinations.

Suitable combination partners for the BCDs are preferably algicides, such as diuron, dichlorophen, endothal, fentin acetate or quinoclamine, molluscicides, such as fentin acetate, metaldehyde, methiocarb, niclosamide, thiodicarb and trimethacarb, fungicides, such as dichlofluanid, tolylfluanid, iodopropargyl butylcarbamate, fluorfolpet and azoles, such as tebuconazole or conventional antifouling active compounds, such as 2-(N,N-dimethylthiocarbamoylthio)-5-nitrothiazyl, tetrabutyldistannoxane, 2-tert-butylamino-4-cyclopropylamino-6-methylthio-1,3,5-triazine, 4,5-dichloro-2-n-octyl-4-isothiazolin-3-one, 2,4,5,6-tetrachloroisophthalodintrile, tetramethylthiuram disulphide, 2,4,6-trichlorophenylmaleimide, 2,3,5,6-tetra-chlor-4-(methylsulphonyl)-pyridine, diiodomethylparatryl sulphone, thiabendazole, tetra-phenylboron-pyridine salt, and the copper and sodium salt of 2-pyridinethiol 1-oxide.

The BCDs in their use in antifouling conmpositions furthermore comprise the customary constituents, such as are described, for example, in Ungerer, Chem. Ind. 37 (1985), 730–732 and Williams, Antifouling Marine Coatings 1973, Park Ridge: Noyes 1973.

In addition to the active compounds mentioned or their combinations, antifouling compositions therefore comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene rubbers, butadiene/acrylonitrile rubbers, butadiene/styrene/acrylonitrile rubbers, drying oils, such as linseed oil, asphalt and epoxide compounds, resin esters or modified hard resins in combination with tar or bitumens, small amounts of chlorinated rubber, chlorinated polypropylene and vinyl resins.

If appropriate, the antifouling compositions also comprise inorganic pigments, organic pigments or dyestuffs, which are preferably insoluble in sea water. The antifouling compositions can furthermore comprise materials such as colophony, in order to allow controlled release of the active compounds or of the active compound combinations. The antifouling compositions can furthermore comprise plasticizers, modifying agents which influence the rtheological properties and other conventional constituents. The compounds of the formula (I) or abovementioned combinations can also be incorporated into self-polishing antifouling systems.

The antifouling composition preferably comprises the BCDs in concentrations of 1 to 20% by weight.

The compositions according to the invention advantageously allow the compositions available to date to be replaced by more effective compositions. They show a good stability and advantageously have a broad action spectrum.

EXAMPLE 1

A 2% strength solution of N-cyclohexyl-benzothiophene-2 -carboxamide S,S-dioxide is added in various dilutions to still liquid minerl salt agar.

After solidification of the agar, 1 ml of the liquid mineral salt medium is additionally pipetted onto the agar and the plates are inoculated with the alga Oscillatoria tenuis. After an incubation period of 2 weeks at room temperature under irradiation with light, the growth of the alga was rated.

No alga growth was detected at concentrations from 20 ppm

What is claimed is:

1. A method for protecting an object from fouling by at least one species selected from the group consisting of species of the groups Lepadomorpha, Balanomorpha and sessile Entomostraca, or by a combination of said at least one species and another organism capable of fouling said object, said method comprising apply to said object an antifouling effective amount of a compound of formula (I):

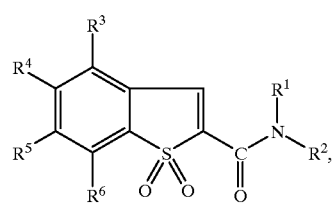

in which $R^1$ represents optionally substituted alkyl, or represents alkenyl or alkinyl, or represents in each case optionally substituted cycloalkyl or cycloalkylalkly, or represents in each case optionally substituted aralkyl, aralkenyl, aralkinyl or aryl, $R^2$ represents hydrogen, or represents optionally substituted alkyl, or $R^1$ and $R^2$, together with the nitrogen atom to which they are bonded, represent an optionally substituted heterocyclic radical and $R^3$, $R^4$, $R^5$ and $R^6$ independently of one another each represent hydrogen, halgen, cyano, nitro, alkyl, alkoxy, alkylthio, halogenoalkyl, halogenoalkoxy or halogenoalkylthio.

2. The method according to claim 1 wherein the object is to be protected from fouling by Cirripedia.

* * * * *